(12) United States Patent
Metelski

(10) Patent No.: US 6,364,268 B1
(45) Date of Patent: Apr. 2, 2002

(54) CEILING MOUNT

(75) Inventor: Andreas Metelski, Romanshorn (CH)

(73) Assignee: Leica Microsystems AG, Heerbrugg (CH)

( * ) Notice: Subject to any disclaimer, the term of this patent is extended or adjusted under 35 U.S.C. 154(b) by 0 days.

(21) Appl. No.: 09/608,344

(22) Filed: Jun. 29, 2000

(30) Foreign Application Priority Data

Jul. 3, 1999 (CH) .............................................. 1225/99

(51) Int. Cl.[7] ................................................. A47H 1/10
(52) U.S. Cl. ...................... 248/317; 248/278.1; 359/368
(58) Field of Search ............................... 248/317, 325, 248/331, 280.11, 281.11, 282.1, 284.1, 278.1; 280/35, 47.35, 651; 359/369, 368, 384, 382, 377

(56) References Cited

U.S. PATENT DOCUMENTS

| | | | | |
|---|---|---|---|---|
| 2,775,481 A | * | 12/1956 | Mitchell | 299/58 |
| 3,265,087 A | * | 8/1966 | Livingston | 137/560 |
| 4,544,121 A | * | 10/1985 | Komura | 248/331 |
| 4,881,709 A | * | 11/1989 | Nakamura | 248/281.1 |
| 5,377,371 A | * | 1/1995 | Foster | 5/503.1 |
| 6,095,468 A | * | 8/2000 | Chirico et al. | 248/282.1 |
| 6,186,458 B1 | * | 2/2001 | Hansen | 248/274.1 |
| 6,213,481 B1 | * | 4/2001 | Marchese et al. | 280/35 |

OTHER PUBLICATIONS

Leica Product Brochure, "WILD M680" Surgical Microscope System, Copyright 1993.

* cited by examiner

*Primary Examiner*—Ramon O. Ramirez
*Assistant Examiner*—A. Joseph Wujciak
(74) *Attorney, Agent, or Firm*—Simpson, Simpson & Snyder, PLLC

(57) ABSTRACT

The invention refers to a novel ceiling mount having two vertical supports which effect decoupling of the vibration behavior of a microscope mount and an auxiliary mount, the auxiliary mount receiving an equipment box which contains a computer, a control system, and/or an energy source. The invention further concerns a novel interface for mounts having a damping element, and an adjusting apparatus for correcting the position of an action circle plane of a microscope.

37 Claims, 10 Drawing Sheets

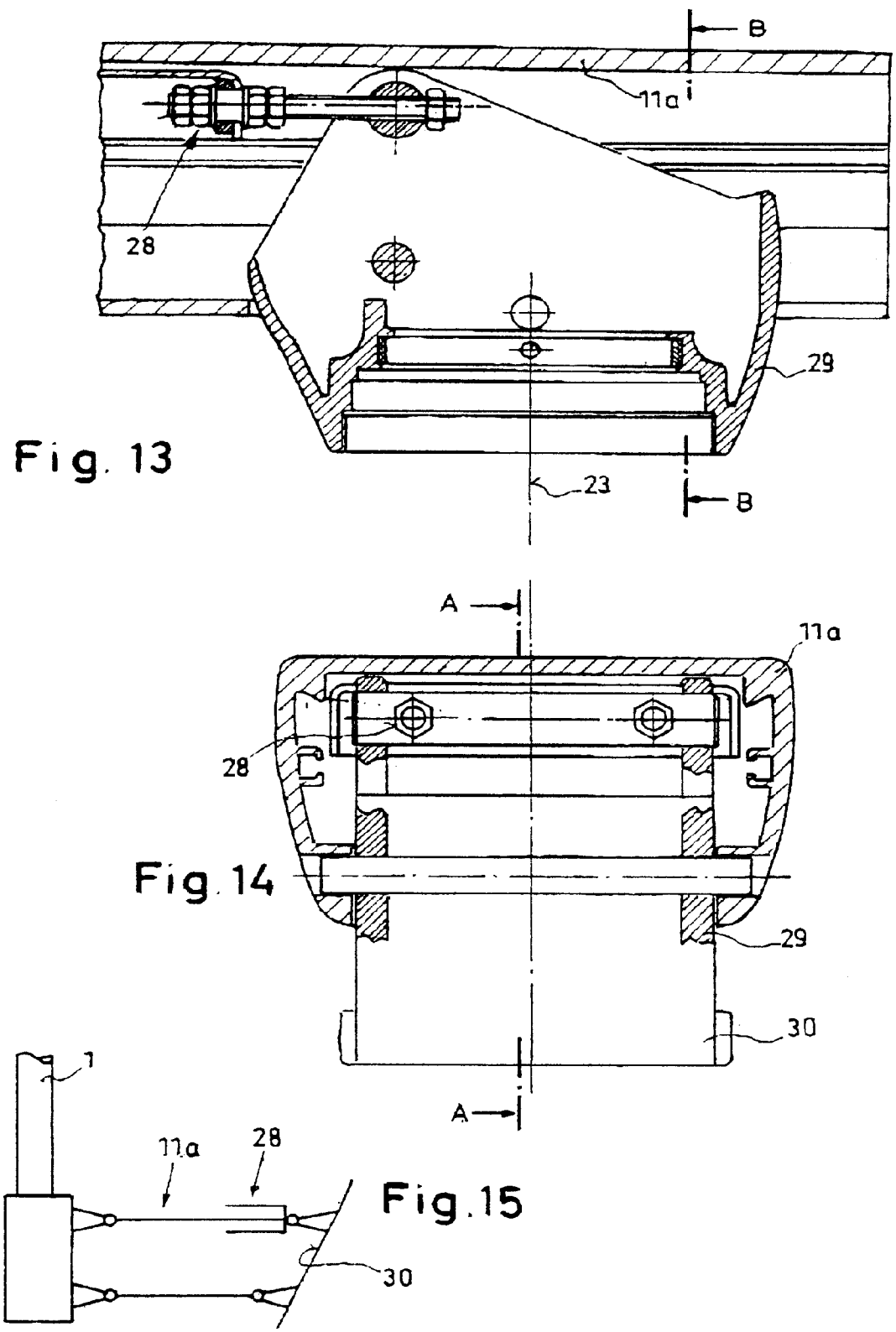

CEILING MOUNT

CROSS REFERENCE TO RELATED APPLICATIONS

This invention disclosed herein claims priority of a Swiss patent application CH 1225/99.

FIELD OF THE INVENTION

This invention relates to a ceiling mount for a microscope, in particular a surgical microscope.

BACKGROUND OF THE INVENTION

Ceiling mounts are used in a very wide variety of applications, and are differently configured depending on the different application requirements.

One major application area is intensive care medicine, in which medical devices, trays, instrument holders, etc. must be maneuverable with as much flexibility as possible in the vicinity of the patient.

The Dräger company has marketed, under product names including "Movita,™" "Ondal,™" "Julian,®" and "Sola,™" a series of ceiling mounts that used in intensive medicine and intensive care.

Ceiling mounts are also known, however, in the field of surgical microscopy, in which they are used principally in cases in which the surgical area is stationary, i.e. the surgical microscope does not leave the room.

In contrast to conventional floor stands, which usually are of a displaceable configuration, ceiling mounts are often fixed in position at one point (the attachment point on the ceiling, usually a ceiling console). The weight of the entire structure, and any tilting torques, are absorbed at that point.

Displaceable floor stands, on the other hand, often have a counterweight that balances out the weight of the microscope and of the support arms holding it by way of a vertical column, so that it does not tip over. In an earlier stand (MS-C™) of the Applicant, see brochure WILD M680 Short overview of functions, printed in 1993, an equipment box with the control system and energy supply system for the microscope was used as part of the counterweight. This box was mounted on the vertical column of the strand, and a mechanism prevented the box and the microscope from projecting in one direction on the same side, could have caused the stand to tip over.

Since modern microscopes require control and energy supply systems placed in a comparable equipment box, when designing a ceiling mount the question arises as to how the equipment box is to be mounted.

A simple solution would be to place the equipment box on the floor in the vicinity of the microscope. This would, inter alia, reduce weight at the ceiling attachment point. On the other hand, however, the absence of the weight of the equipment box or of another counterweight on the ceiling mount would result in an asymmetrical tilting load on the ceiling console, since it then carries only the microscope and its support arms on one side. The effect, known per se, of weight compensation through the vertical (i.e. the column, in the case of floor stands) is absent.

Another mounting possibility would be to suspend the equipment box on the ceiling mount, so that a configuration comparable to a floor stand (MS-C™) would result. The disadvantages would then be, however, that the equipment box would be mounted directly on the vertical or on the vertical support. The equipment box would then be either near the ceiling (with the disadvantage of poor operability) or at operating height (with the disadvantage of interfering in the core area of the operating theater). The advantage of a ceiling mount, namely a large overhead working range and little interference with personnel in the core area of the operating theater, would thereby be limited.

A vibration problem would also result, since if the equipment box were moved, the vibrations thereby produced would necessarily be passed on to the microscope; and conversely, movements of the microscope would cause vibratory excitation of the equipment box that then might be coupled back in.

SUMMARY OF THE INVENTION

The object of the invention is therefore, as a first problem, to integrate the microscope and equipment box onto the ceiling mount without exhibiting the disadvantages recited above.

This problem is solved by way of two inventive steps: First, the equipment box has allocated to it a separate horizontal compensating arm on which it—usually projecting from the microscope—is pivotable about a vertical; and second, there is also allocated to the equipment box a separate vertical support which is attached to the ceiling console in addition to the vertical support for the microscope. This support carries the compensating arm.

Although configurations having two or more vertical supports arranged next to one another that were not provided for microscopes are already known from the Dräger ceiling mounts mentioned earlier, the latter were provided for a completely different reason. In such known mounts the vibration problem plays a subordinate role, since it is only when looking through a microscope that a vibration becomes annoying.

The combination of these two steps results in a ceiling mount that offers the least impediment to personnel with the greatest freedom of movement. Leaving this aside, the tilting load on the ceiling mounting point can be minimized if the microscope and equipment box are positioned diametrically opposite one another through the vertical. If the horizontal compensating space is moreover pivotable via a horizontal axis or is telescopically extendable, operability and the freedom of movement of personnel are greatly improved.

On the other hand, however, the separation between the microscope and microscope supports and the equipment box and equipment box supports also results in a reduction in manual vibratory influences, so that the new configuration according to the present invention achieves all the aforesaid objects merely by way of its basic structure.

The above object is achieved by a ceiling mount which comprises a ceiling console, a first vertical support and a microscope, a second vertical support is attached to the ceiling console and is parallel to the first vertical support, an auxiliary mount is carried by the second vertical support, and a counterweight is attached to the auxiliary mount.

Particular embodiments and developments are recited in the dependent claims.

Advantageously, the compensation arm of the equipment box is pivotable in a vertical plane, as is the horizontal support arm of the microscope, and/or a telescopic vertical support arm could also enhance operability.

If necessary, the equipment box itself is also pivotable about a vertical axis on its suspension from the compensation arm, which also increases user-friendliness.

Advantageously, the horizontal support arm of the microscope is furthermore subdivided into at least two portions, so that the horizontal support arm can in itself also be bent about at least one vertical and/or about at least one horizontal, thus resulting in more movement capabilities and positioning capabilities in space for the microscope.

Preferably a control panel and a display—remote from the equipment box—are furthermore mounted on a separate console in the region of the microscope. They can be attached, for example, to the wall of the room or to the horizontal support arm of the microscope.

Another object of the invention, however, is a further critical improvement in vibration behavior, which can also in itself be regarded as independent of the aforementioned objects since it relates also to configurations without an equipment box, and in fact to floor stands and wall stands.

The problem of vibration damping is a general one in stand design. In the "OHS" designed by the Applicant and now also on the market, good damping properties were achieved by a particular configuration of and choice of material for the support and also, in particular, by a particular choice of materials for damping support feet with respect to the floor. In the case of a ceiling mount, however, the vibration behavior is fundamentally different, since the ceiling mount is rigidly attached to a building element. The theories of vibration feedback through insufficiently damping support feet were fundamentally inapplicable here. It was also, of course, impossible to provide damping support feet.

This object is therefore achieved by another inventive step that can also be used advantageously in other ceiling mounts or even in floor stands:

The inventor has recognized that the new ceiling mount, in the absence of a damping capability with respect to a fixed building element, should have at least one damping interface in its extent proceeding from the fixed building element that is in itself modular configuration and on the one hand has damping layers or properties known per se but on the other hand also has non-damping layers. Only the combination of damping and non-damping layers at the interfaces of the mount according to the present invention yielded the desired successful damping.

A configuration of this kind according to the present invention is recited in claim 7, which is worded as a dependent claim as already mentioned but whose subject matter can also be utilized independently. It use is not limited to ceiling mounts, but rather can also be advantageously used in other types of stand.

The interface according to the present invention fundamentally makes it possible for different vibration processes to take place before and after it, which in fact ideally compensate for one another.

Further dependent claims describe further developments and particular embodiments.

For example, the arrangement of the damping layers at horizontal interfaces of the subdivided horizontal support has proven favorable.

According to a particular embodiment, the rigid and elastic are integrated with one another to form a sandwich element. This can also easily be replaced if necessary, or replaced by other elements having different damping properties.

Instead of elastomeric damping layers, the following dampers can also, for example, be used in the context of the invention: cup spring packets with damping surfaces rubbing against one another, or pneumatic or hydraulic damping cushion rings with cross-section-reducing connecting tubes.

Different elastomeric or nonelastomeric damping layers or segments could also be joined to one another for this purpose. They can be arranged, for example, in orifices of a sandwich element with stem-shaped damping elements. Better surface pressure can result therefrom.

A preferred material composition is recited in claim 10. Damping layers of the company styled Getzner Werkstoffe GmbII (Bürs-Bludenz, Austria), with the designations "Sylomer®HD 1006E" and "Sylomer® HD 906E" were used in the preferred exemplary embodiments.

Particularly good vibration damping results if at least one of the support arms is configured as a parallelogram, and is supported or damped with a diagonally extending gas spring.

The new configuration with a multi-part horizontal arm as indicated above also, however, like other earlier configurations from the existing art, exhibited a further unpleasant problem (inherently independent of the one above) that is also to be solved by the present invention.

Because of the limited rigidity of a horizontal microscope support arm, when this horizontal support arm is bent about a vertical pivot axis, the weight of the further support arm and of the microscope results in torsion in the support arm that is mounted on the vertical support. This torsion causes the microscope to sink. laterally relative to the position of the microscope when the horizontal arms are stretched out. Since the action circle of the peripheral weight (the microscope) about the bending axis thus lies on a non-horizontal plane, the microscope necessarily (assuming good bearings with low bearing frictional forces) drifts out of position in the unbraked state until the microscope has reached its lowest point.

This is unpleasant if the user expects positional accuracy from a microscope. One obvious action would be limit this problem by inserting electric brakes around the vertical axis in question. This would mean an additional outlay for equipment, however, and would also disadvantageously increase the weight of the mount.

More detailed examinations of known mount configurations, for example those of the aforementioned Dräger series, offer no solutions, since with these ceiling mounts the pivotability about the vertical does not meet to be smooth to the same degree as is required by comparison, in surgical microscope mounts. Greater frictional forces in the pivot bearings, however, prevent the unit from drifting out of position, so that with known intensive-care medicine ceiling mounts the aforementioned problem did not even occur. What is specifically demanded from microscope mounts, however is the following: when the brakes are released the unit must not drift, but should be particularly easy to move.

According to the present invention, this object is achieved in surprisingly simple fashion by the fact that the action circle plane is pivoted by suitable design measures into an at least approximately horizontal position. The starting point in this context is preferably a normal working position of the mount or microscope in which it is most often used.

A configuration of this kind according to the present invention, which can certainly also be used independently of the configurations recited above (e.g. for wall and floor stands as well), is recited in claim 14.

In order to allow directionally independent adjustment, care must be taken when adjusting the action circle that the absolute torsion angle α of the twisting horizontal microscope support arm out of the horizontal is the same on each side of the support arm, i.e. that the angle α, viewed from the end of the support arm, is identical in mirror-symmetrical fashion whether the support arm is bent to the left or right.

Particular embodiments and developments of this inventive idea are received in further dependent claims.

The result of an oblique position of the most recently mentioned vertical rotation axis is that when the horizontal arm is in a stretched-out position, the load (the microscope) comes to rest just as far down as when the one horizontal subsupport is bent and torsion is thus triggered; this is one of the preferred solutions.

Since the torsion angle depends on the weight of the microscope and its accessories, it is preferable to select an average value at an average working weight (average potential energy) for the accessories and equipment.

Further developments of the invention are recited in further dependent claims.

It is a further object of the invention to provide a surgical microscope which provides good damping properties and the necessary equipment of the microscope should not interfere with the viewing or operating field of the user.

The above object is achieved by a surgical microscope with a ceiling mount which comprises a ceiling console, a first vertical support and a microscope mount which has at least one support arm for carrying the microscope, a second vertical support is attached to the ceiling console and is parallel to the first vertical support, an auxiliary mount is carried by the second vertical support, and a counterweight is attached to the auxiliary mount.

Further embodiments of the invention are disclosed by the dependent claims.

All the claims, together with the descriptive introduction and the description of the Figures below, and with the Figures and the list of reference characters, recite the disclosure of the invention in all its aspects. The text portions are replaceable and expandable.

BRIEF DESCRIPTION OF THE DRAWINGS

The subject matter of the invention is described with reference to the embodiments shown in the drawings.

FIG. 13 shows a section along A (FIG. 14) through a different action circle tilt adjustment system of the microscope mount;

FIG. 14 shows a section B through the action circle tilt adjustment system as shown in FIG. 13;

FIG. 15 shows a diagram of the action circle tilt adjustment system of FIGS. 13 and 14;

DETAILED DESCRIPTION OF THE INVENTION

Figure 1:
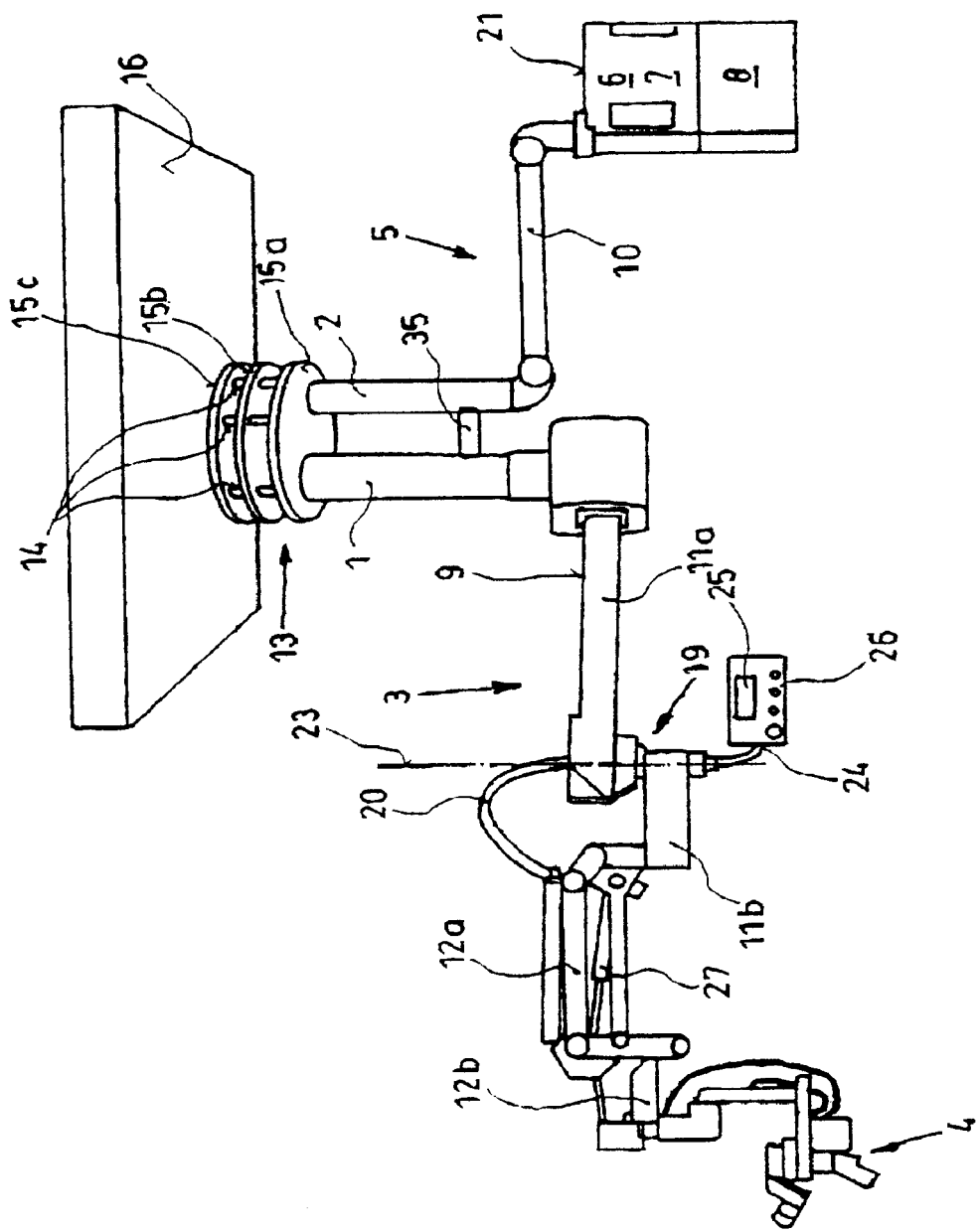
FIG. 1 shows a ceiling mount according to the present invention in the extended state.
Figure 2:
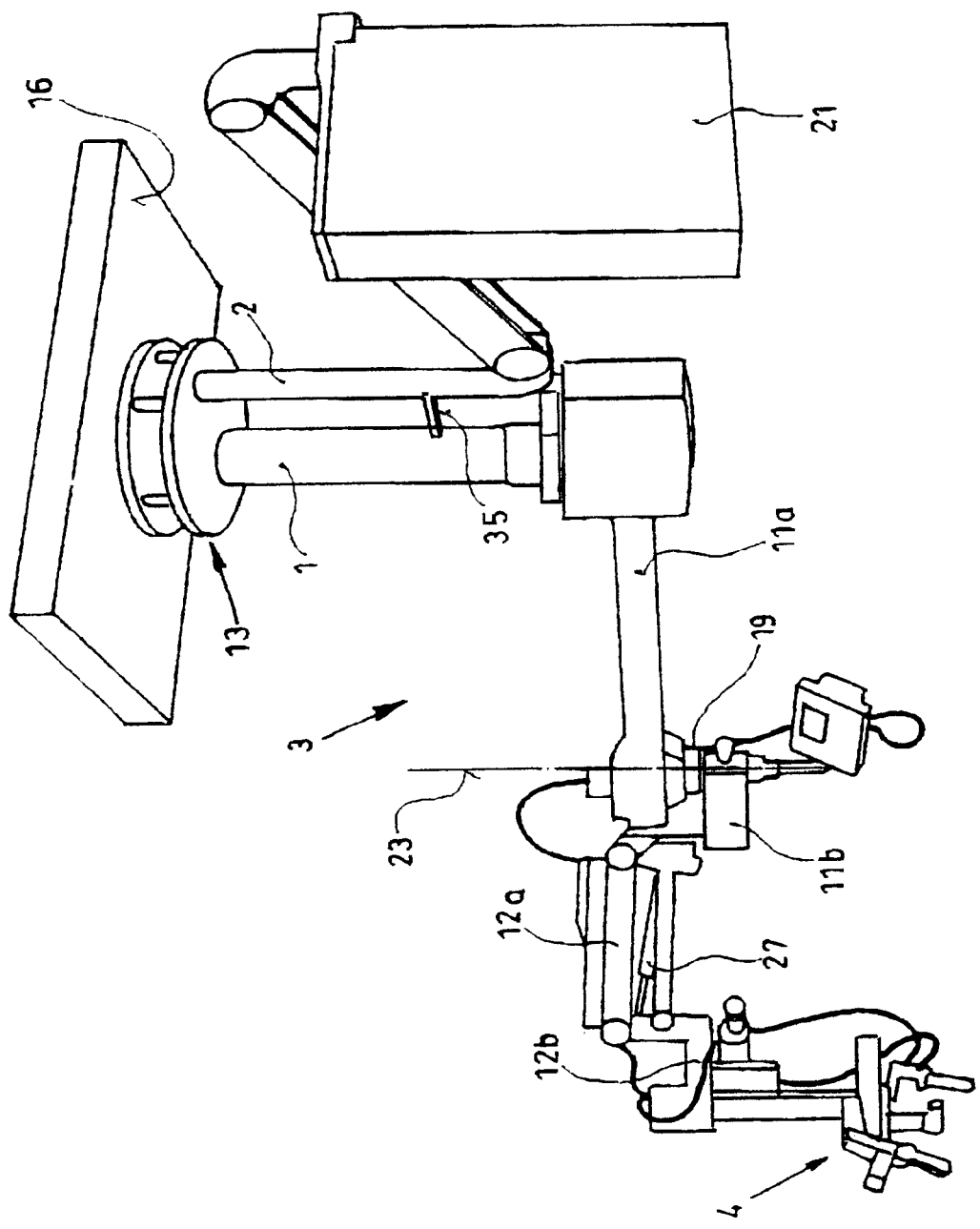
FIG. 2 shows the mount according to FIG. 1 with the equipment box raised and pivoted, and the microscope mount pivoted slightly.

The Figures are described in overlapping fashion. Identical reference numbers denote identical or similar components having identical functions. Reference numbers with indices belong to parts that are made up of multiple elements. The Figures are understood simply as possible exemplary embodiments, and do not limit the patent scope.

The preferred embodiment of the new ceiling mount has two vertical supports 1, 2 that are mounted, independently of one another, on a ceiling console 13. The one support 1 carries the actual microscope mount 3 having a surgical microscope 4; the other support 2 carries an auxiliary mount 5 having an equipment box 21 that also (when box 21 is correctly positioned) serves as a counterweight and contains, for example, a computer 6, control system 7, and energy sources 8 or energy converters. "Energy sources" are also understood in particular to be, for example, light sources that send light through a glass fiber cable 20 a microscope 4. Glass fiber cable 20 is guided, together with all other control lines, from equipment box 21 via a bridge 35 between the two supports 1 and 2 from auxiliary mount 5 to microscope mount 3.

Figure 3:
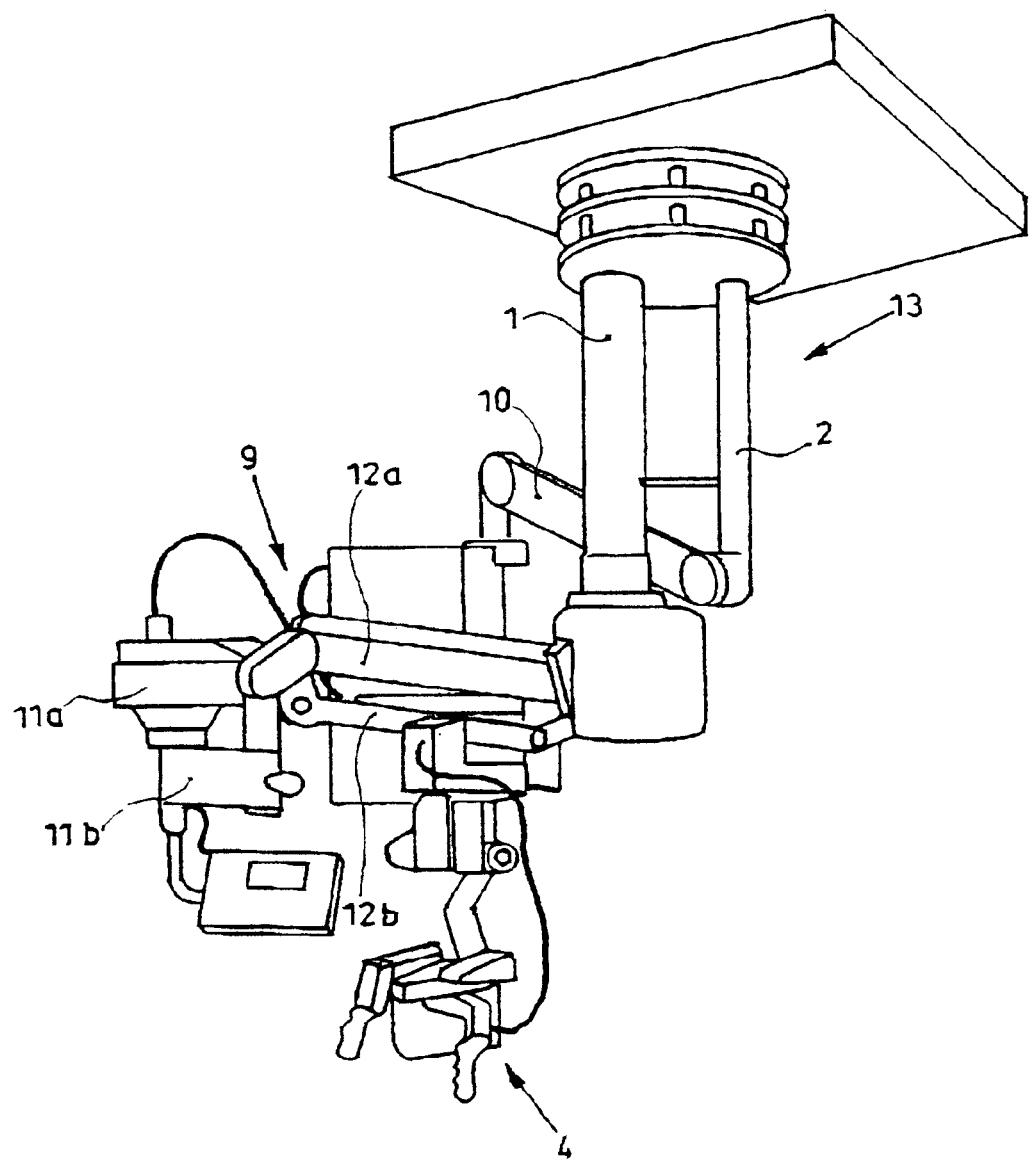
FIG. 3 shows the mount according to FIG. 1 folded up in the smallest possible state.
Figure 4:
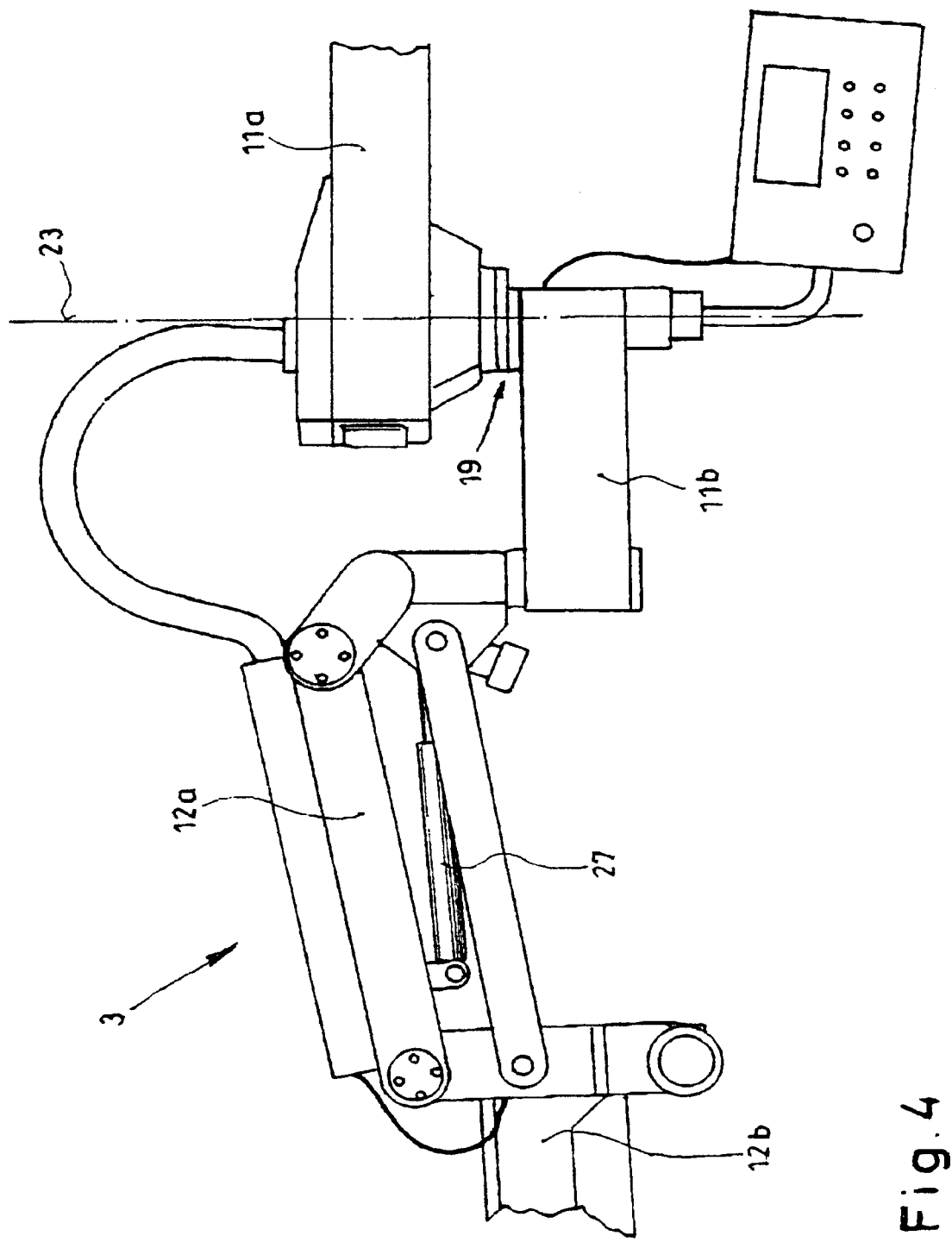
FIG. 4 shows a detail of the microscope mount.
Figure 5:
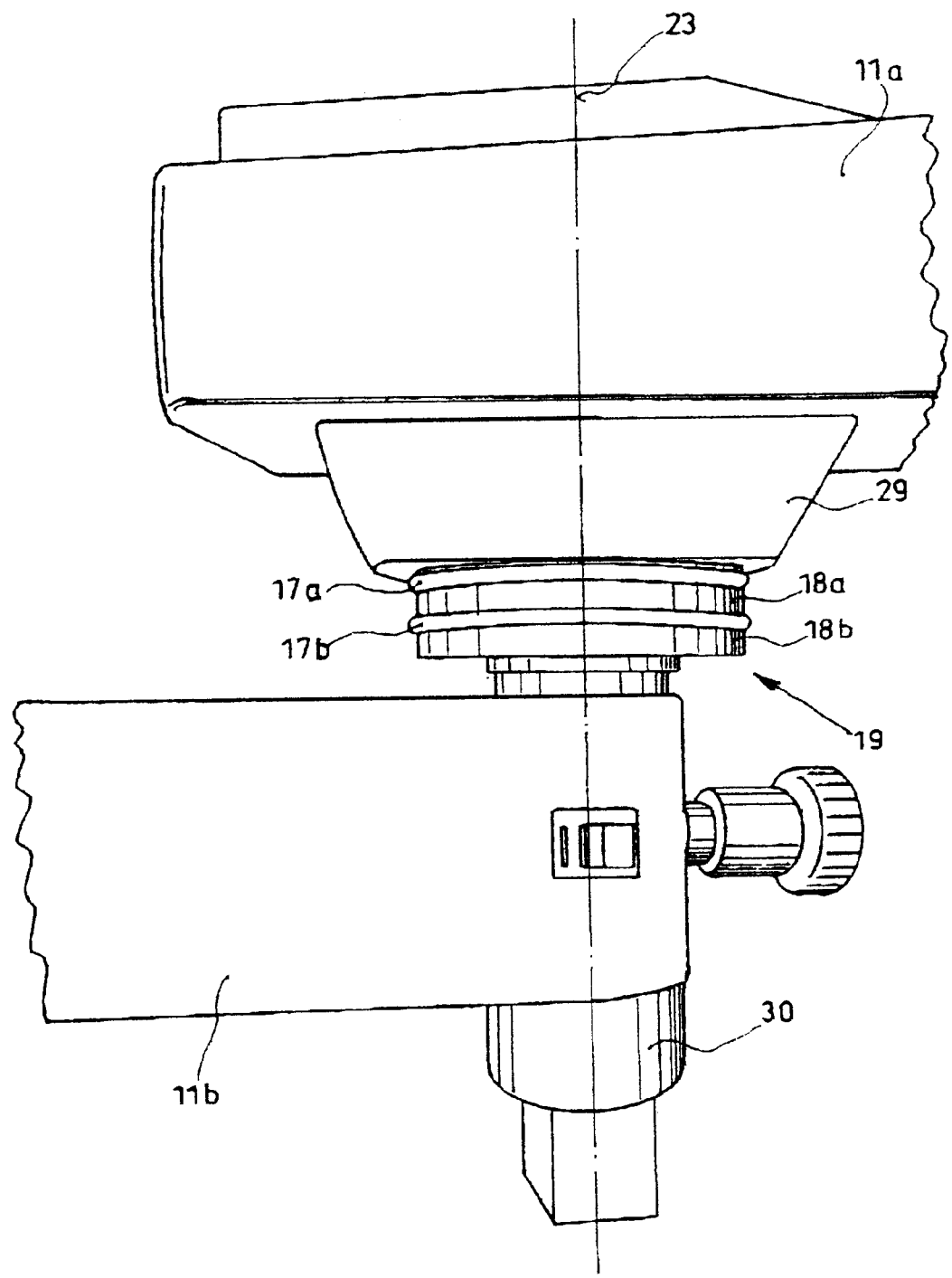
FIG. 5 shows an enlarged detail with a damping interface installed.

Microscope mount 3 and auxiliary mount 5 comprise a horizontally oriented support arm 9 and compensating arm 10, respectively. Support arm 9 for surgical microscope 4 is subdivided into at least two support arm elements, joined articulatedly to one another, each of which is subdivided once again into 11a and 11b, and 12a and 12b, while compensating arm 10 receives the counterweight or equipment box 21 and generally holds it at a suitable distance from surgical microscope 4. Only when necessary can the entire configuration also be folded up so that microscope 4 and equipment box 21 end up directly next to one another (parked position) (FIG. 3). This can be, for example, a restocking position or, if necessary, a position in which the user many perform manipulations on the equipment box while simultaneously also looking through the microscope. In these infrequent instances, the balance function of the two mount parts (microscope mount and auxiliary mount) are dispensed with, and the load is accordingly also absorbed asymmetrically by ceiling console 13.

The advantages or effect of the configuration according to the present invention generally results, inter alia, in a fundamentally small asymmetrical load on ceiling console 13, which substantially comprises multiple vertical columns 14 and at least one horizontal support plate 15 (in the present case three support plates 15) which receive vertical supports 1, 2.

This is because as a rule, horizontal arm 9 and compensating arm 10 projecting from supports 1, 2 are located opposite one another, so that the loads pertaining to each one are suspended symmetrically on an imaginary vertical proceeding from the center of ceiling console 13. This not only relieves stress on the ceiling installation device 13, but also, according to the present invention, provides vibration decoupling and separation of the various masses.

In particular, the position of equipment box 21 can be changed without transferring the vibrations necessarily associated therewith to surgical microscope 4.

The further problem solved by the invention is the inevitable drifting out of position of a weight on the two support arm elements 11a, b and 12a, b, which are pivotable with respect to one another about at least one vertical axis 23, the first part of support arm element 11a (held on vertical support 1) being pivotable about vertical support 1. The problem arises from the finite rigidity of support arms, which have the tendency to bend and twist slightly under the load of the weight (surgical microscope 4). Because of this bending, the center of gravity of microscope 4 drops somewhat lower than it should be based on the mathematical principles of optimum supports. What then occurs, however, when one of the two support arm elements 11b is bent with respect to the other 11a about axis 23, is a weight moment that can result in "drift", i.e. pivoting of surgical microscope 4 to its lowest point (with lower potential energy) along its action circle.

The solution according to the present invention to this "drift" problem is a simple technical trick: based on a knowledge of the mechanical bending properties of microscope mount configurations 3, at least vertical axis 23 is tilted out of the vertical, so that depending on the bending of the two adjacent support arm elements 11a, b and 12a, b with respect to one another, the result is to "horizontalize" the outer support arm element 11b or 12a,b projecting from the inner support arm element 11a. As a result, the center of gravity of the load is held in its potentially correct position (same vertical position), and laterally acting force components cannot even occur. The action circle of the microscope is thus moved into a horizontal plane.

The preferred configuration for "horizontally" the action circle is depicted in detail in FIG. 5 and FIGS. 13 through 15. In this context, support arm element 11a receives a pivot element 29 which contains axis 23. Pivot element 29 is pivotable relative to support arm element 11a by way of an adjustment system 28 having a tie rod and nuts. Axis 23 can thus easily be adjusted about the vertical. Since pivot element contains, in the assembled state, a shaft 30 on which second support arm element 11b is mounted, its tilt can be adjusted. It is thus also possible to adjust the position of the action circle relative to the horizontal.

As an alternative to an adjustment system 28, the angle of an axis with respect to the vertical can also be set obliquely a priori.

Figure 6:
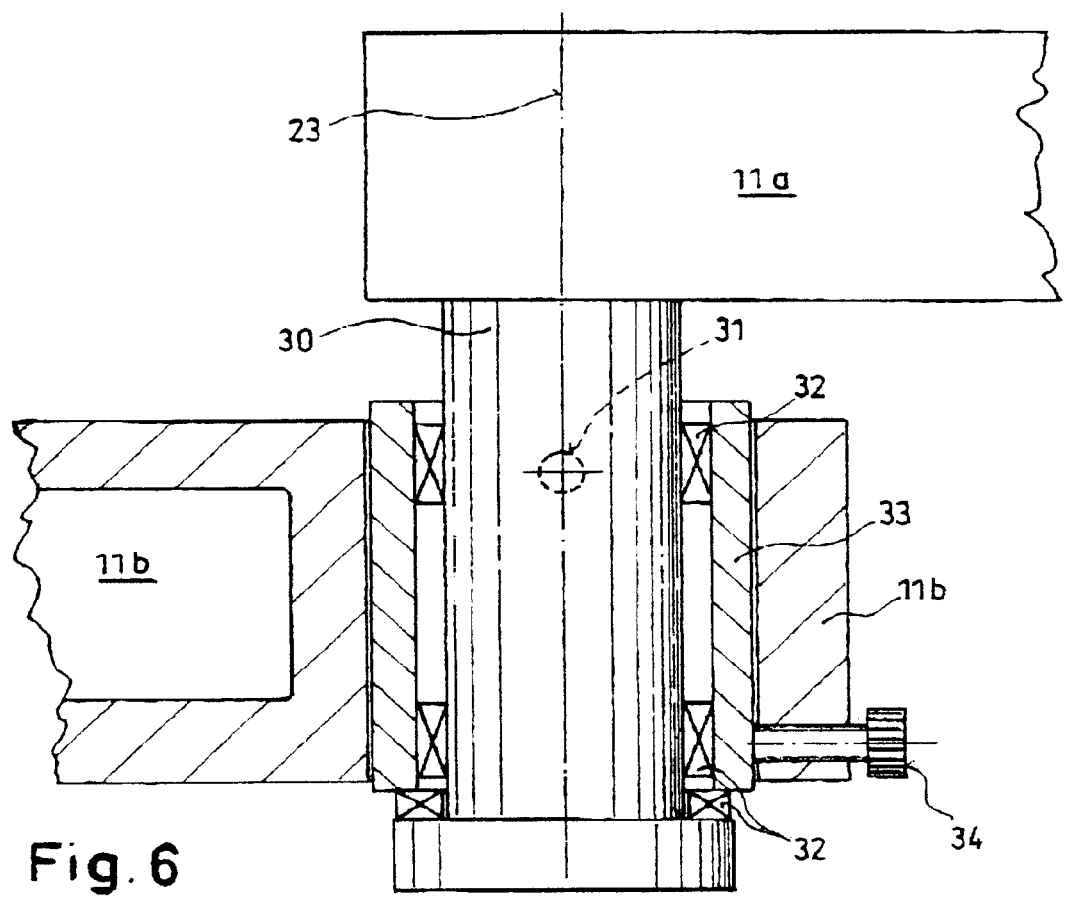
FIG. 6 shows a diagram of an action circle tilt adjustment system of the microscope mount, in section.
Figure 7:
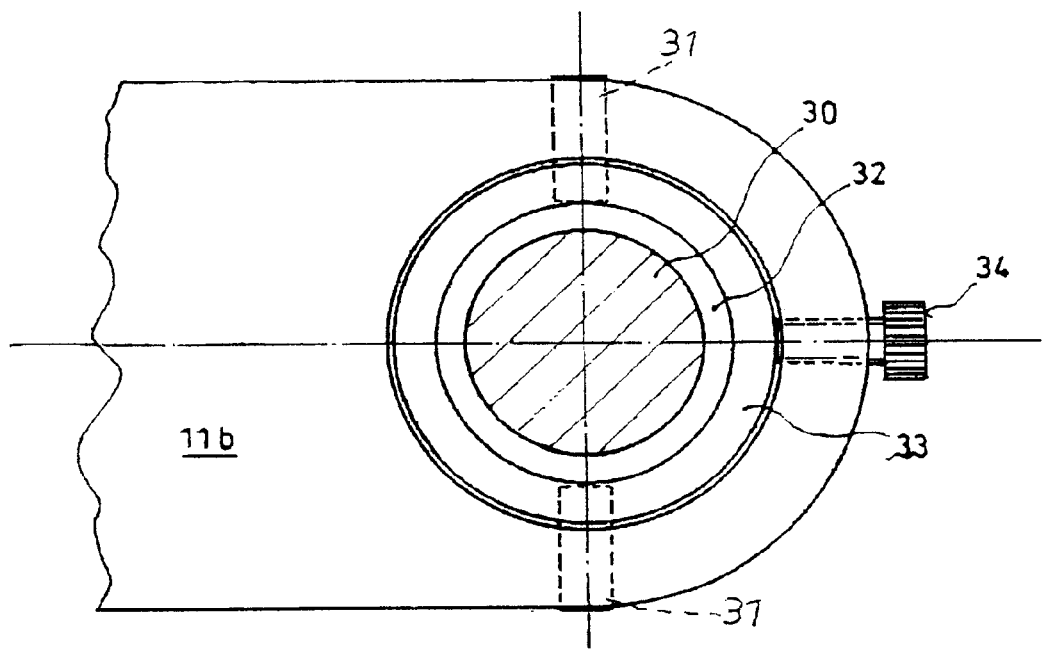
FIG. 7 shows a plan view of the configuration as shown in FIG. 6.
Figure 8:
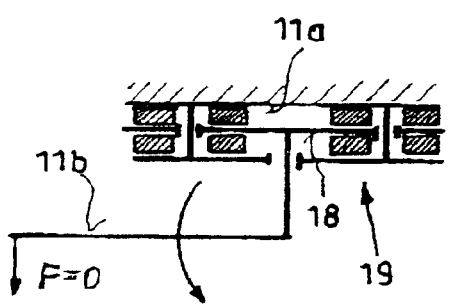
FIG. 8 shows a diagram of a damping interface in section, in the unloaded state.
Figure 9:
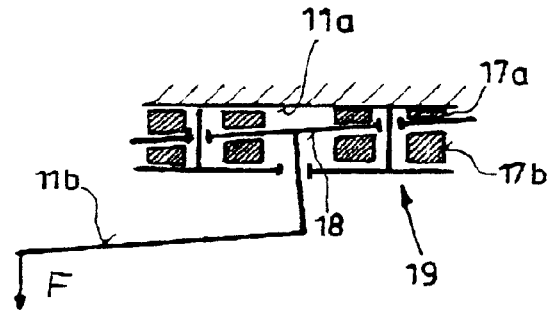
FIG. 9 shows the diagram of FIG. 8 in the loaded state.
Figure 10:
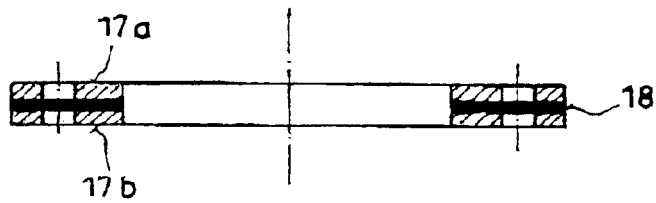
FIG. 10 shows a section along B (FIG. 12) through a damping element according to the present invention.
Figure 11:
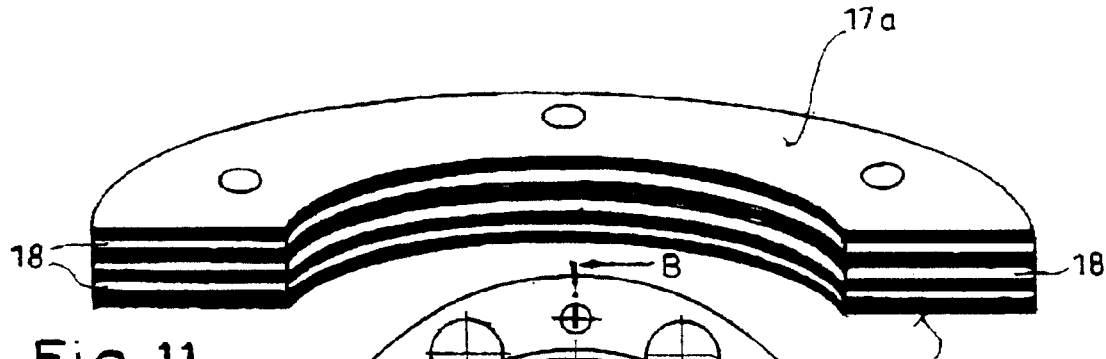
FIG. 11 shows one half of a different damping element according to the present invention with a sandwich design.
Figure 12:
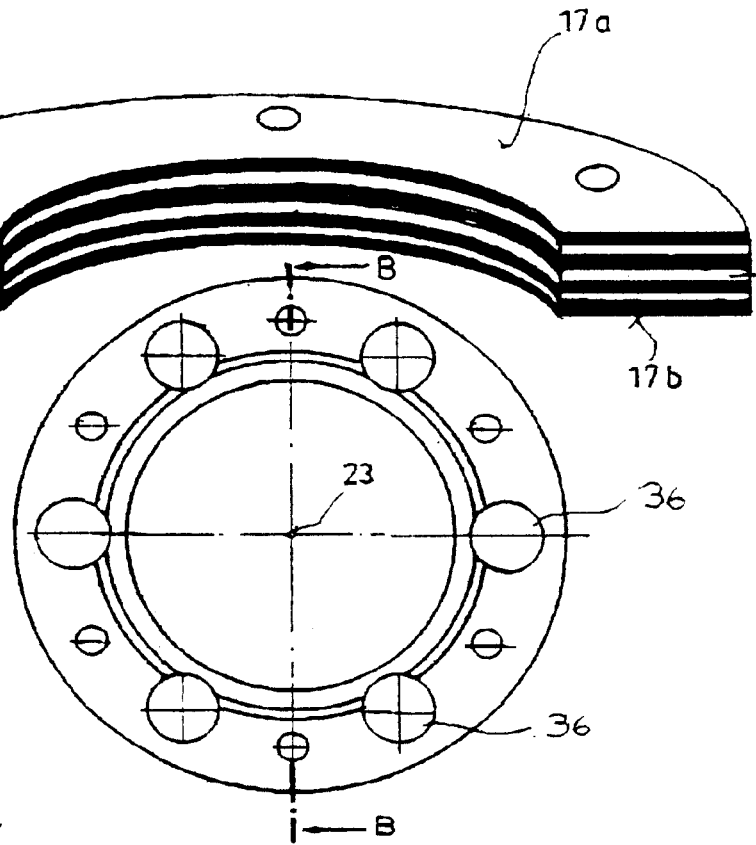
FIG. 12 shows a plan view of the damping element of FIG. 10.
Figure 16:
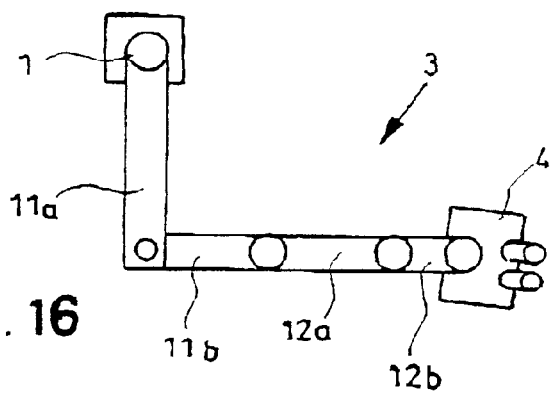
FIG. 16 shows a plan view of a schematic microscope mount, bent to the right.
Figure 17:
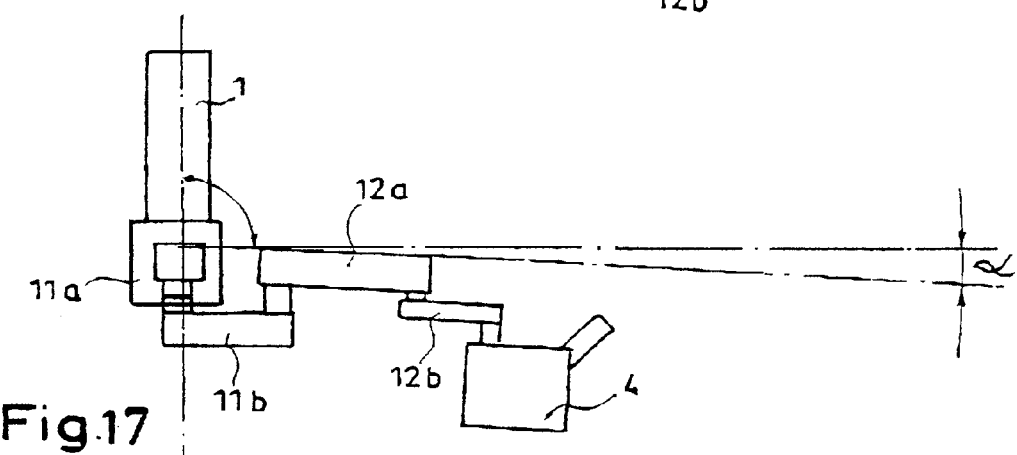
FIG. 17 shows a side view of the microscope mount in the position shown in FIG. 16.
Figure 18:
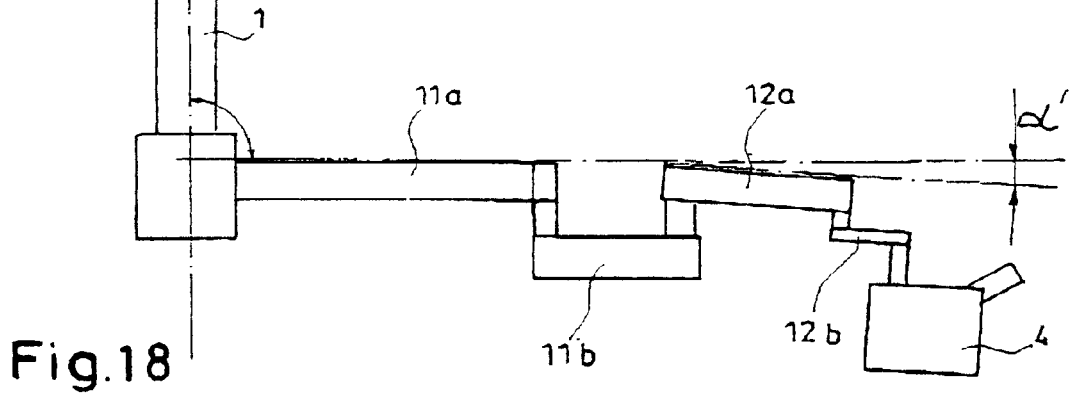
FIG. 18 shows a side view, rotated 90°, of the same microscope mount with support arms 11 and 12 extended.
Figure 19:
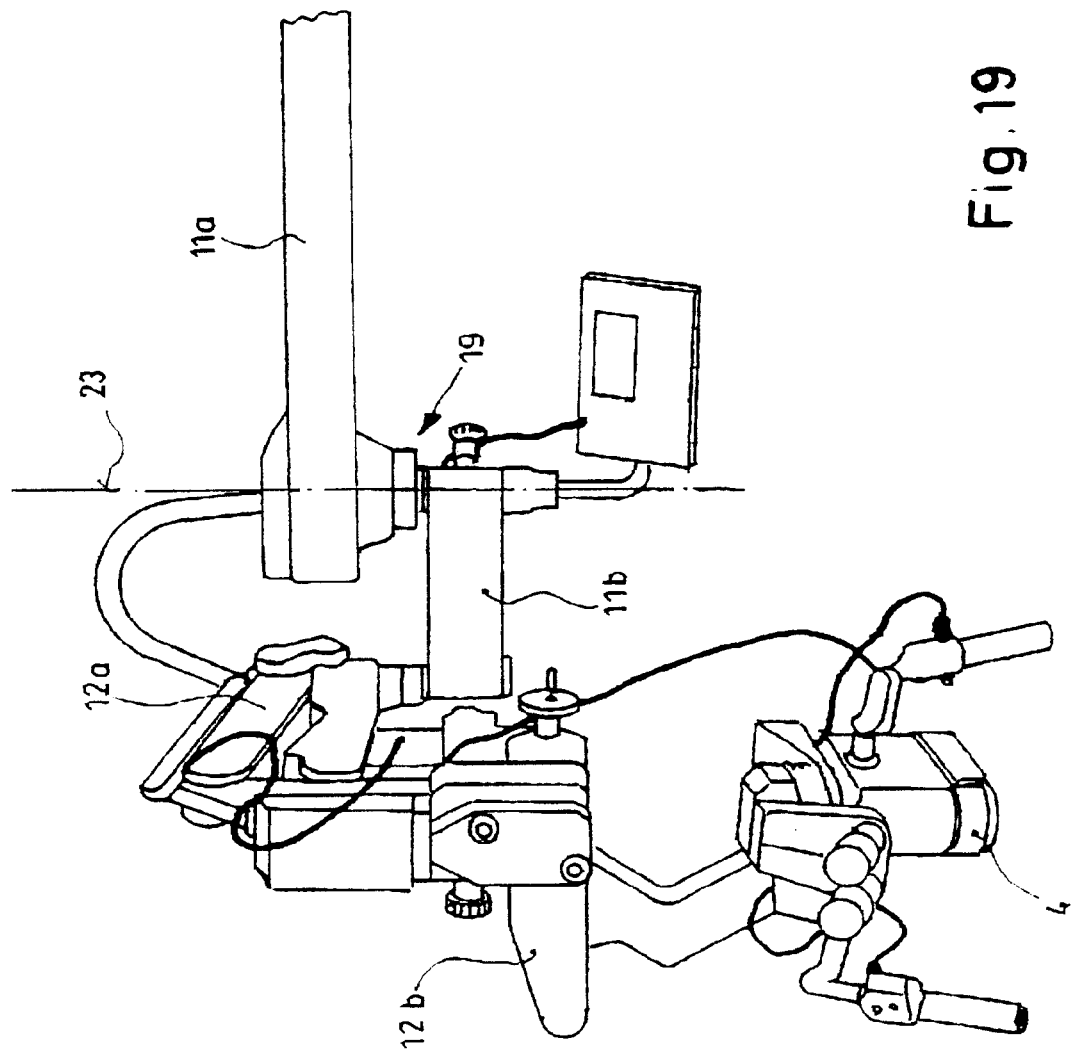
FIG. 19 shows a stand as shown in FIG. 1 in the preferred working position, with support arms 11a, b and 12a, b bent three times.

A variant of this configuration is depicted schematically in FIGS. 6 and 7:

In this variant, shaft 30 is joined rigidly to support arm element 11a. It carries a bearing sleeve 33 that is mounted in easily rotatable fashion with respect to shaft 30 by way of bearing 32. Sleeve 33 is mounted rotatably with respect to support arm element 11b by the fact that it is mounted in the latter on a gimbal suspension 31. An adjusting screw 34 allows adjustment of the tilt of sleeve 33 relative to support arm element 11b, and thus of the relative tilt adjustment of axis 23 about a vertical.

This invention has been disclosed with respect to certain embodiments. It is clear that modifications and amendments can be made by a skilled person without departing from the scope of the claims below.

PARTS LIST

1 Vertical support for microscope mount
2 Vertical support for auxiliary mount
3 Microscope mount
4 Surgical microscope
5 Auxiliary mount
6 Computer
7 Control system
8 Energy source
9 Support arm
10 Compensating arm
11 Support arm elements a, b
12 Distal support arm elements a, b
13 Ceiling console
14 Support column
15 Support plate
16 Fixed building element, ceiling
17 Damping layers a, b, c
18 Non-damping layers a, b, c
19 Damping interface, damping element
20 Glass fiber cable
21 Equipment box
22 Bridge
23 Vertical axis
24 Console
25 Display
26 Operating elements
27 Gas spring
28 Adjusting means
29 Pivot element
30 Support shaft
31 Gimbal suspension
32 Bearing
33 Bearing sleeve
34 Adjusting screw
35 Bridge
36 Damping stem

What is claimed is:

1. A ceiling mount for a microscope comprising a ceiling console, a first vertical support mount to said ceiling console, a microscope mount connected to said first vertical support and having at least one horizontal support arm which carries the microscope, a second vertical support attached and parallel to the first vertical support, an auxiliary mount carried by the second vertical support, and a counterweight attached to the auxiliary mount.

2. The ceiling mount as defined in claim 1, wherein an equipment box forms the counterweight.

3. The ceiling mount as defined in claim 1, wherein the auxiliary mount has at least one compensating arm that is pivotable with respect to the second vertical support about its axis and preferably in a vertical plane.

4. The ceiling mount as defined in claim 1, wherein the support arm comprises at least two support arm elements that are movable, connected to one another to allow movement of the microscope in all dimensions.

5. The ceiling mount as defined in claim 4, wherein at least one of said support arm elements is configured as a parallelogram support that is preloaded by way of a diagonally retained gas spring.

6. The ceiling mount as defined in claim 1, wherein a console with a display and an operating element for the microscope is mounted on a wall defined by a room the microscope is positioned in.

7. The ceiling mount as defined in claim 6, wherein the console with the display and operating elements for the microscope is mounted on one of the support arm elements.

8. The ceiling mount as defined in claim 1, wherein the support arm or support arm elements have at least one interface with one another that is equipped in damping fashion, such that for each interface, preferably at least two plies of damping layers are separated by at least one non-damping layer.

9. The ceiling mount as defined in claim 8, wherein the damping and non-damping layers form a sandwich element.

10. The ceiling mount as defined in claim 8, wherein the interface has at least one damping layer in an approximately horizontal position.

11. The ceiling mount as defined in claim 8, wherein resilient and vibration-damping elements are arranged at a least one interface between support arms or support arm elements and the resilient and vibration-damping elements consist essentially of cup springs with friction surfaces, pneumatic damping cushions, hydraulic damping cushions and damping stems.

12. The ceiling mount as defined in claim 8, wherein at least one layer of an elastomeric damping material is provided at at least one interface having the following material properties: a compression of max. 20% of the material thickness under a pressure of 0–2.5 N/mm$^2$.

13. The ceiling mount as defined in claim 1, wherein said at least one support arm is configured as a parallelogram support that is preloaded by way of a diagonally retained gas spring.

14. A ceiling mount for a microscope comprising two adjacent arm elements which are mounted pivotally about a vertical axis such that the microscope describes an action circle about the vertical axis, the action circle lying in an at least approximately horizontal plane, and means for adjusting the action circle tilt such that the potential energy of the load defined by the microscope is approximately identical in all angular positions as dictated by arm configuration and axis layout at least under an average load.

15. The ceiling mount as defined in claim 14, wherein the means for adjusting comprise a tilt adjustment system for the vertical axis and/or a tilt adjustment system for a bearing sleeve suspended in gimbaled fashion.

16. The ceiling mount as defined in claim 15, wherein the action circle tilt adjustment system is operable by the user.

17. The ceiling mount as defined in claim 14, wherein the adjustment of the action circle tilt is achieved for average microscope weight and for the most common microscope position.

18. The ceiling mount as defined in claim 14, wherein said ceiling mount further comprises a first support and a second support extending parallel to one another, a microscope mount connected to said first support, an auxiliary mount connected to said second support, and a bridge for the passage of cables arranged between said first support and said second support.

19. A surgical microscope with a ceiling mount comprising a ceiling console, a first vertical support mounted to said ceiling console, a microscope mount connected to said first vertical support and having at least one support arm for carrying the microscope, a second vertical support attached to the ceiling console and parallel to the first vertical support, an auxiliary mount carried by the second vertical support and having at least one compensating arm that is pivotable with respect to the second vertical support about its axis and in a vertical plane, and a counterweight attached to the auxiliary mount.

20. The surgical microscope as recited in claim 19 has an equipment box which forms the counterweight.

21. The surgical microscope as defined in claim 19, wherein the support arm comprises at least two support arm elements that are movable connected to one another to allow movement of the microscope in all dimensions.

22. The surgical microscope as defined in claim 21, wherein at least one of said support arm elements is configured as a parallelogram support that is preloaded by way of a diagonally retained gas spring.

23. The surgical microscope as defined in claim 22, wherein the means for adjusting comprise a tilt adjustment system for the vertical axis and a tilt adjustment system for a bearing sleeve suspended in gimbaled fashion.

24. The surgical microscope as defined in claim 22, wherein the adjustment of the action circle is achieved for average microscope weight and for most microscope positions.

25. The surgical microscope as defined in claim 22, wherein the action circle tilt adjustment system is operable by the user.

26. The surgical microscope as defined in claim 25 wherein the bridge is covered.

27. The surgical microscope as defined in claim 19, wherein a console with a display and an operating element for the microscope is mounted on a wall defined by a room the surgical microscope is positioned in.

28. The ceiling mount as defined in claim 27, wherein the console with the display and operating elements for the surgical microscope is mounted on one of the support arm elements.

29. The ceiling mount as defined in claim 19, wherein the support arm or support arm elements have at least one interface with one another that is equipped in damping fashion, such that for each interface, preferably at least two plies of damping layers are separated by at least one non-damping layer.

30. The surgical microscope as defined in claim 29, wherein the damping and non-damping layers form a sandwich element.

31. The surgical microscope as defined in claim 29, wherein the interface has at least one damping layer in an approximately horizontal position .

32. The surgical microscope as defined in claim 29, wherein resilient and vibration-damping elements are arranged at at least one interface between support arms or support arm elements and the resilient and vibration-damping elements consist essentially of cup springs with friction surfaces, pneumatic damping cushions, hydraulic damping cushions and damping stems.

33. The surgical microscope as defined in claim 29, wherein at least one layer of an elastomeric damping material is provided at at least one interface having the following material properties: a compression of max. 20% of the material thickness under a pressure of 0–2.5 N/mm$^2$.

34. The surgical microscope as defined in claim 29 comprises two adjustment arm elements which are mounted pivotally about a vertical axis such that the surgical microscope describes an action circle about the vertical axis, the action circle lies in at least an approximately horizontal plane and the potential energy of the load defined by the surgical microscope is approximately identical in all angular positions, this is determined by the arm configuration and axis layout at least under an average load, and means for adjusting the action circle.

35. The surgical microscope as defined in claim 19, wherein said at least one support arm is configured as a parallelogram support that is preloaded by way of a diagonally retained gas spring.

36. The surgical microscope as defined in claim 19 wherein a bridge for the passage of cables or the like is arranged between a first support and a second support and the bridge is arranged between auxiliary mount and microscope mount.

37. The surgical microscope as defined in claim 19, wherein at least one vertical axis deviates from the vertical.

* * * * *

UNITED STATES PATENT AND TRADEMARK OFFICE
CERTIFICATE OF CORRECTION

PATENT NO.     : 6,364,268 B1
DATED          : April 2, 2002
INVENTOR(S)    : Metelski It is certified that error appears in the above-identified patent and that said Letters Patent is hereby corrected as shown below:

Column 8,
Lines 43-44, change "a first vertical support mount to said ceiling console" to -- a first vertical support mounted to said ceiling console --

Signed and Sealed this

Third Day of September, 2002

*Attest:*

*Attesting Officer*

JAMES E. ROGAN
*Director of the United States Patent and Trademark Office*